United States Patent
Maxson et al.

(10) Patent No.: US 11,166,732 B2
(45) Date of Patent: Nov. 9, 2021

(54) DEVICES AND METHODS FOR PERFORMING ANTERIOR CRUCIATE LIGAMENT RECONSTRUCTION USING PATIENT-SPECIFIC DRILL GUIDE

(71) Applicant: Biomet Manufacturing, LLC, Warsaw, IN (US)

(72) Inventors: William Maxson, Ponte Vedra, FL (US); Kevin T. Stone, Winona Lake, IN (US); Jason D. Meridew, Warsaw, IN (US); Nathan M. Sautter, North Manchester, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 210 days.

(21) Appl. No.: 16/314,156

(22) PCT Filed: Jul. 7, 2017

(86) PCT No.: PCT/US2017/041186
§ 371 (c)(1),
(2) Date: Dec. 28, 2018

(87) PCT Pub. No.: WO2018/009860
PCT Pub. Date: Jan. 11, 2018

(65) Prior Publication Data
US 2019/0231371 A1    Aug. 1, 2019

Related U.S. Application Data

(60) Provisional application No. 62/360,119, filed on Jul. 8, 2016.

(51) Int. Cl.
*A61B 17/17* (2006.01)
*A61B 17/16* (2006.01)
(Continued)

(52) U.S. Cl.
CPC ...... *A61B 17/1714* (2013.01); *A61B 17/1633* (2013.01); *A61B 17/1764* (2013.01);
(Continued)

(58) Field of Classification Search
CPC .................. A61B 17/1714; A61B 17/1764
See application file for complete search history.

(56) References Cited

U.S. PATENT DOCUMENTS

| 5,300,077 | A |   | 4/1994 | Howell |
| 6,019,767 | A | * | 2/2000 | Howell ............ A61B 17/1714 |
|           |   |   |        | 606/88 |

(Continued)

FOREIGN PATENT DOCUMENTS

| EP | 1550418 A1 | 7/2005 |
| WO | WO-2010121147 A1 | 10/2010 |
| WO | WO-2018009860 A1 | 1/2018 |

OTHER PUBLICATIONS

"International Application Serial No. PCT/US2017/041186, International Search Report dated Sep. 18, 2017", 6 pgs.

(Continued)

*Primary Examiner* — Nicholas W Woodall
(74) *Attorney, Agent, or Firm* — Schwegman Lundberg Woessner, P.A.

(57) ABSTRACT

A guide for drilling a tunnel in a knee joint having intercondylar roof and tibial eminence. The guide can comprise a guide assembly having a positioning member including an inferior end, and a guide arm extending from the positioning member including a trochlear tip; and a drill sleeve having a body attached to the inferior end, an aperture extending along a drilling axis, and a distal end having a patient-specific surface configured to engage an anterior surface of the tibia. A method of producing a tibial tunnel can comprise inserting a trochlear tip of a guide arm between the tibial eminence and the intercondylar roof, adjusting a position of (Continued)

a positioning member connected to the guide arm, engaging a patient-specific tip of a drill sleeve connected to the positioning member with a surface of a tibia, and inserting a drill bit through the drill sleeve to drill a tibial tunnel.

15 Claims, 8 Drawing Sheets

(51) Int. Cl.
*A61B 34/10* (2016.01)
*A61B 17/00* (2006.01)
*A61B 17/56* (2006.01)

(52) U.S. Cl.
CPC .... *A61B 34/10* (2016.02); *A61B 2017/00477* (2013.01); *A61B 2017/568* (2013.01); *A61B 2034/108* (2016.02)

(56) References Cited

U.S. PATENT DOCUMENTS

| | | |
|---|---|---|
| 6,254,604 B1 | 7/2001 | Howell |
| 6,254,605 B1 * | 7/2001 | Howell ............. A61B 17/1714 606/86 R |
| 10,098,646 B2 * | 10/2018 | Ardito ............. A61B 17/1714 |
| 2010/0298894 A1 * | 11/2010 | Bojarski ............. A61B 34/10 606/86 R |
| 2011/0092804 A1 | 4/2011 | Schoenefeld et al. |
| 2012/0310399 A1 | 12/2012 | Metzger |

OTHER PUBLICATIONS

"International Application Serial No. PCT/US2017/041186, Written Opinion dated Sep. 18, 2017", 7 pgs.

"European Application Serial No. 17740265.8, Response to Communication pursuant to Rules 161(1) and 162 EPC filed Sep. 17, 2019", 14 pgs.

* cited by examiner under 35 U.S.C. 371 from International Application Serial No. PCT/US2017/041186, filed on Jul. 7, 2017, and published as WO 2018/009860 A1 on Jan. 11, 2018, which claims the benefit of priority of Maxon et al., U.S. Provisional Patent Application Ser. No. 62/360,119, entitled "ACL METHOD," filed on Jul. 8, 2016, each of which is hereby incorporated by reference herein in its entirety.

DEVICES AND METHODS FOR PERFORMING ANTERIOR CRUCIATE LIGAMENT RECONSTRUCTION USING PATIENT-SPECIFIC DRILL GUIDE

CROSS-REFERENCE TO RELATED PATENT DOCUMENTS

This patent application is a U.S. National Stage Application

TECHNICAL FIELD

The present application pertains generally, but not by way of limitation, to devices and methods for reconstruction of a torn or otherwise damaged anterior cruciate ligament (ACL). More specifically, but not by way of limitation, the present application relates to guide devices for drilling a tibial tunnel in the reconstruction of an anterior cruciate ligament using arthroscopic or endoscopic techniques, as well as a method for using such devices.

BACKGROUND

Numerous improvements in repairing damage to knee joints have been made over the years, and some of the major advances involve the use of endoscopic techniques and arthroscopic procedures. Endoscopic techniques have also been developed for use in repair and reconstruction of damaged anterior cruciate ligaments.

The ACL is a three-dimensional structure with broad attachments and a continuum of fibers. These fibers are of different lengths, have different attachment sites, and are under different tensions. Although many current substitutes for cruciate ligaments may not duplicate the complex orientation and operation of normal ACLs, they can operate to mimic the normal ACL operation effectively when they are placed isometrically. "Isometrically" positioned means that the length of the substitute ligament will not change during angular movement of the tibia relative to the femur; the distance between the affixed ends of the ligament remains a constant. Isometric placement can maximize the number of fibers that can be taut throughout the range of motion of the knee and allows for early knee motion without generating high ligament strains.

Correct isometric positioning of the ACL graft can be an important factor for a successful operation; isometrically placed grafts can provide the most stable knees. Correct isometric placement can reproduce corresponding femoral and tibial anatomic attachment sites and will allow an ACL graft to mimic the normal ACL. Non-isometric graft placement can result in plastic deformation of the ACL substitute, postoperative laxity, abnormal kinematics, or failure of fixation.

The importance of accurate placement of the graft tunnels and ACL substitute can be shown by the fact that graft placements sometimes only several millimeters apart can produce significantly different strains in the cruciate substitute. A placement of the ACL origin or insertion which is too anteriorly placed in the knee joint can result in a ligament that is taut in flexion, but lax in extension. Posterior placement can cause the ligament to be taut in extension, but lax in flexion. Isometric tunnel placement can provide effective stability throughout the range of motion. Therefore, one of the challenges during anterior cruciate ligament replacement procedures can be the accurate isometric placement of the tibial tunnel. Another challenge during anterior cruciate ligament replacement can be the accurate placement of the tibial tunnel relative to the longitudinal axis of the tibia. In this regard, it has been determined that the medial or lateral orientation of the tibial tunnel relative to the longitudinal axis of the tibia should also be taken into consideration.

The preparation of the intercondylar notch can also be important as is the proper positioning and placement of the femoral and tibial tunnels. Accurate and sufficient notchplasty can prevent impingement of the graft which could cause failure or significant complications. Often today the amount and degree of notchplasty is determined during an operation by "feel" or experience. This frequently results in more of the bone in the notch being removed than is necessary, or in less of the bone being removed than is required necessitating later correction in the operation.

Another related challenge in the ACL replacement procedure can be to minimize the amount of bone removed from the femoral intercondylar roof to prevent impingement during extension. Correct placement of the tibial tunnel can prevent abrasive wear between the ACL graft and the intercondylar roof while minimizing the extent of roofplasty required to avoid impingement. This can result in time and effort savings, and maximizes the desirable feature of preserving the maximum amount of natural bone in the knee. It is another goal of ACL replacement procedures to create tibial tunnel placement that may allow the implanted ACL to interact more normally with the posterior cruciate ligament (PCL).

Examples of ACL repair instrumentation are described in U.S. Pat. No. 5,300,077 to Howell, and U.S. Pat. No. 6,254,604 to Howell, which are hereby incorporated by reference herein in their entirety.

Overview

The present inventors have recognized, among other things, that a problem to be solved can include inaccurate positioning of a tibial tunnel using standard or non-custom ACL repair instrumentation. For example, fixed-axis devices involve judgment from the surgeon in positioning the device against the bone. Furthermore, even if the surgeon decides on suitable bone locations for positioning the device, the selected bone locations might not have suitable topography for mating with contact points of the device. Thus, the device can become slightly misaligned and the resulting drilled tibial tunnel can be slightly misaligned from the desired tibial tunnel axis, can be too short to promote bone growth, and can undesirably interfere with the tibial eminence. Furthermore, fixed-axis devices might to too long or too short to fit patients of different sizes, thereby introducing a potential error point in the placement process.

The present subject matter can help provide a solution to this problem, such as by providing ACL repair instrumentation having patient-specific features that improve the accuracy of tibial tunnel placement. The patient-specific features can include patient-specific surfaces that permit devices, such as drill guides, to be placed precisely on a location of the tibia in only one location, such as at a location determined preoperatively from medical images. The patient-specific features can also include patient-specific dimensions and angles of the device that are incorporated into the device as-manufactured to precisely fit the specific patient. Additionally, the patient-specific features can include adjustable dimensions and angles that can be adjusted to fit the specific patient based on preoperative planning and imaging.

In an example, a drill guide can be used for drilling a tibial tunnel in a knee joint having a femur with an intercondylar roof and a trochlear groove, and a tibia having a tibial eminence. The drill guide can comprise a guide assembly and a drill sleeve. The guide assembly can comprise a positioning member including an inferior end, and a guide arm extending from the positioning member and including a trochlear tip for engaging the intercondylar roof. The drill sleeve can comprise a body attached to the inferior end, an aperture extending along a drilling axis of the body, and a distal end having a patient-specific surface configured to engage an anterior surface of the tibia inferior of the tibial eminence.

In another example, a method of producing a tibial tunnel can comprise inserting a trochlear tip of a guide arm between a tibial eminence of a tibia and an intercondylar roof of a femur, adjusting a position of a positioning member connected to the guide arm proximate a proximal end of the tibia, engaging a patient-specific tip of a drill sleeve connected to the positioning member with a portion of an anterior surface of the tibia proximate the tibial eminence, and inserting a drill bit through the drill sleeve to drill a tibial tunnel in the tibia.

This overview is intended to provide an overview of subject matter of the present patent application. It is not intended to provide an exclusive or exhaustive explanation of the invention. The detailed description is included to provide further information about the present patent application.

Figure 1:
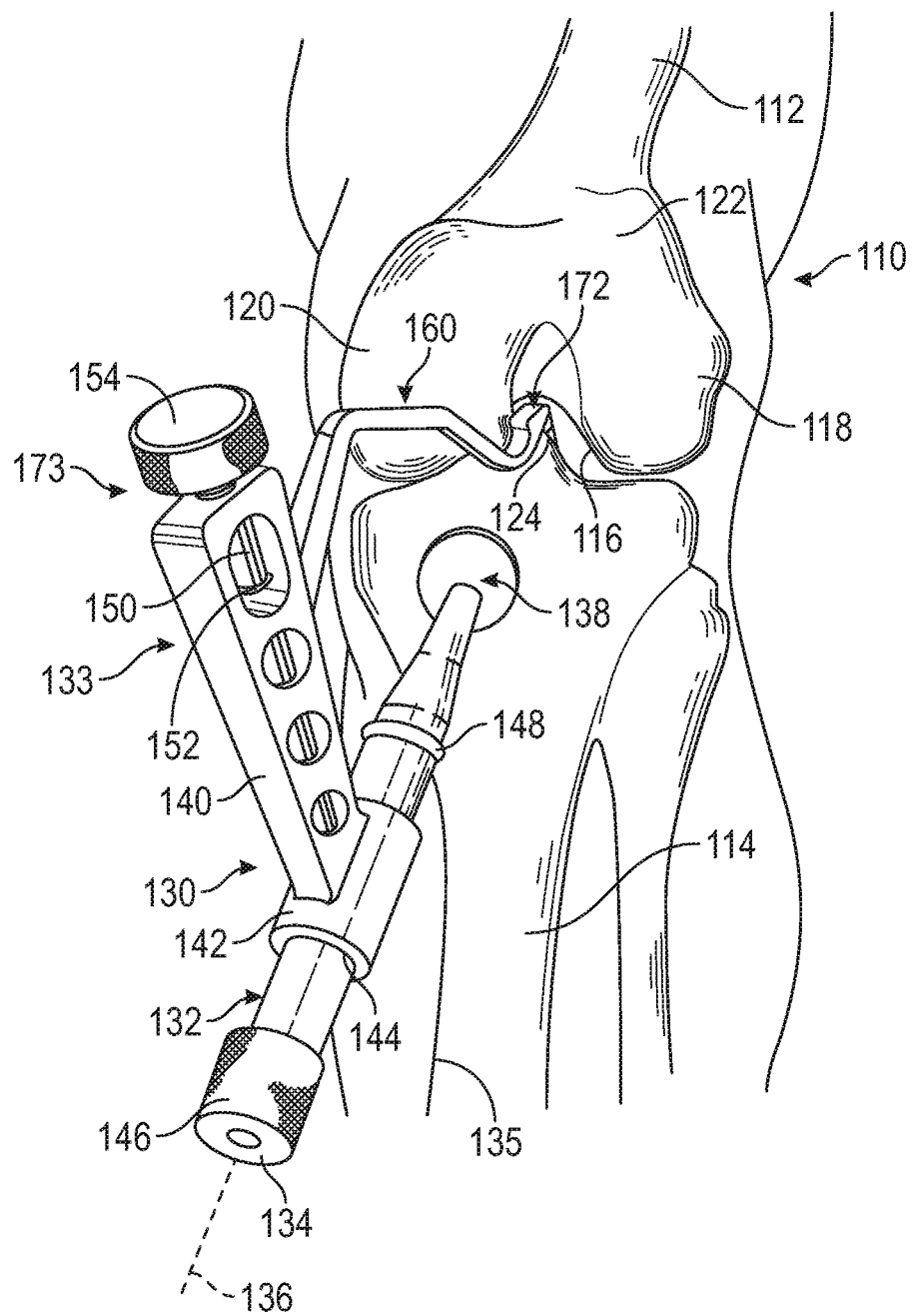
FIG. 1 is a front perspective view of a patient-specific drill guide according to the present disclosure positioned adjacent a tibia in which a tibial tunnel is to be produced.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present teachings provide various patient-specific guides and other instruments for guiding a drilling or cutting device to remove one or more of soft tissue and bone or otherwise prepare the bone for an anterior cruciate ligament (ACL) repair, such as by using a patient-specific ligament, an artificial ligament or the like. Various patient-specific guides according to the present disclosure are illustrated in FIGS. 1-7 and discussed in detail below.

Generally, patient-specific devices, such as patient-specific guides or other instruments and/or patient-specific implants can be designed preoperatively using computer-assisted image methods based on three-dimensional images of the patient's joint and/or adjacent anatomy, as reconstructed from MRI, CT, ultrasound, X-ray, or other medical scans of the patient. Various CAD programs and/or other software can be utilized for the three-dimensional image reconstruction of the anatomy from the medical scans of the patient, such as, for example, software commercially available by Materialise USA, Plymouth, Mich.

Various pre-operative planning procedures related to patient-specific instruments are disclosed in Pub. No. US 2011/0092804 to Shoenefeld et al. entitled "PATIENT-SPECIFIC PRE-OPERATIVE PLANNING" filed on Dec. 20, 2010; and Pub. No. US 2012/0310399 to Metzger entitled "PRE-OPERATIVE PLANNING AND MANUFACTURING METHOD FOR ORTHOPEDIC PROCEDURE" filed on Jun. 6, 2011, which are hereby incorporated by reference herein in their entirety.

In the preoperative planning stage for joint reconstruction, resurfacing or replacement, a preoperative surgical plan is formulated for a specific patient with optional interactive input from the patient's surgeon or other medical professional. Imaging data from medical scans of the relevant anatomy of the patient can be obtained at a medical facility or doctor's office, using any of the medical imaging methods discussed above. The imaging data can include, for example, various medical scans of a relevant joint portion or other relevant portion of the patient's anatomy, as needed for joint or other anatomy modeling and, optionally, for determination of an implant alignment axis or for other alignment purposes. The imaging data thus obtained and other associated information can be used to construct a three-dimensional computer (digital) image of the joint or other portion of the anatomy of the patient, such as, for example, the bones of a knee joint, hip joint, shoulder joint, etc. The three-dimensional digital image of the patient's anatomy is used to formulate the preoperative surgical plan for the patient. The preoperative surgical plan includes the design and construction of patient-specific guides, instruments and/or implants or the selection of non-custom implants and instruments according to surgeon-selected methods of surgical preparation and implantation.

Generally, the patient-specific guides or other instruments (patient-specific devices, for short) of the present teachings are preoperatively configured to match the surface of a bone (with or without cartilage) of a joint of a specific patient and are generally designed and preoperatively configured using computer modeling based on the patient's reconstructed three-dimensional digital image of the patient's knee anatomy. A patient-specific device has a bone engagement surface that is preoperatively configured to conformingly contact and match the corresponding bone surface of the patient (with or without cartilage or other soft tissue), using the reconstructed three-dimensional digital image of the patient's joint anatomy and the computer methods discussed above. In this respect, a patient-specific device can register and nestingly mate with the corresponding bone surface (with or without articular cartilage) of the specific patient in only one position. Accordingly, the patient-specific surface is preoperatively configured as an inverse or mirror or negative or a complementary surface of an outer surface of the corresponding bone, with or without cartilage.

The three-dimensional model of the patient's anatomy can be viewed on a computer display or other electronic screen and can also be reproduced as a hard copy on film or other medium and viewed by direct or indirect or backlight illumination. The model can be sized for viewing on any appropriate screen size and may be cropped, rotated, etc., as selected by the individual (e.g., the surgeon) viewing the screen. The hard copy or models can be used to measure patient-specific lengths and angles useful in customizing various devices.

The patient-specific devices can be manufactured by rapid prototyping methods, such as stereolithography or other similar methods or by CNC milling, or other automated or computer-controlled machining or robotic methods. The patient-specific devices, the implants and optionally other disposable instruments can be packaged and sterilized, and forwarded in a patient- and/or surgeon-specific kit to the surgeon or the surgeon's medical facility for the corresponding orthopedic procedure.

The aforementioned preoperative planning techniques and associated patient-specific devices that can be designed accordingly can be used to design guides and instruments for performing anterior cruciate ligament (ACL) repair procedures. For example, a patient-specific drill guide can be designed and manufactured to include patient-specific surfaces to facilitate the guide mating with anatomy of a specific patient. Additionally, the patient-specific drill guide can be configured to have various dimensions, such as lengths and angles, that facilitate interface between the drill guide and the specific patient for patients of different sized anatomy. As such, patient-specific ACL drill guides can be used to accurately produce longer tibial tunnels in a tibia bone that both improve ligament osseointegration and preserve tibial bone matter.

FIG. 1 is a perspective front view of patient-specific tibial drill guide 130 according to embodiments of the present application in operative association with knee joint 110. Knee joint 110 includes a femur 112 and a tibia 114. Femur 112 is shown to include at its distal end femoral intercondylar notch 116 formed between medial and lateral condyles 118 and 120, respectively. Femur 112 is also shown to include trochlear groove 122 located on the articular cartilage of distal femur 112 where the patella articulates. Tibia 114 is shown to include tibial eminence 124 which is typically a rounded protuberance disposed near the central surface at its proximal end. FIG. 1 also shows tibial drill guide 130 in an inserted position within knee joint 110 prior to its alignment for drilling a tibial tunnel.

Tibial drill guide 130 can comprise drill sleeve 132 and guide assembly 133. Drill sleeve 132 can include aperture 134 that can extend through body 135 along axis 136, tip 138 and knob 146. Guide assembly 133 can include positioning member 140, collar 142, aperture 144, pin 150, aperture 152, thumb screw 154, guide arm 160, guide region 162 and trochlear tip 172.

Figure 2:
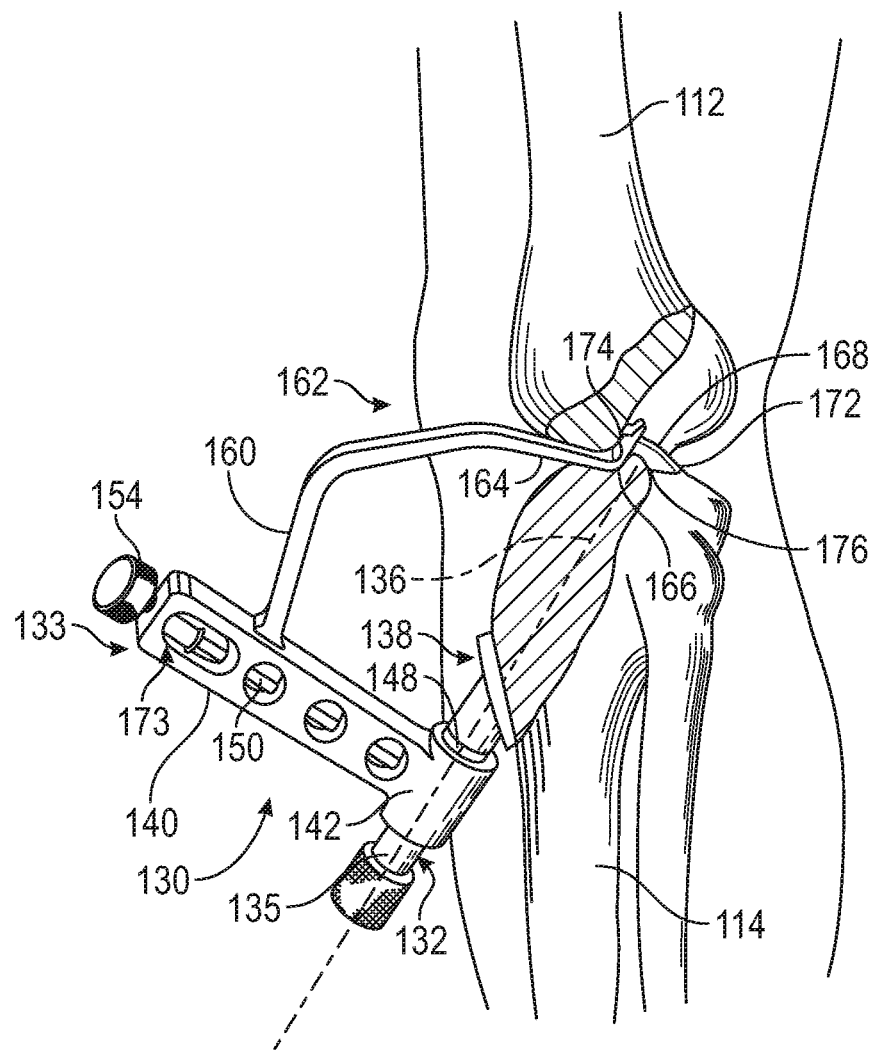
FIG. 2 is a partial cutaway side view of the patient-specific drill guide of FIG. 1 in position for producing a tibial tunnel in a proximal end of the tibia.
Figure 3:
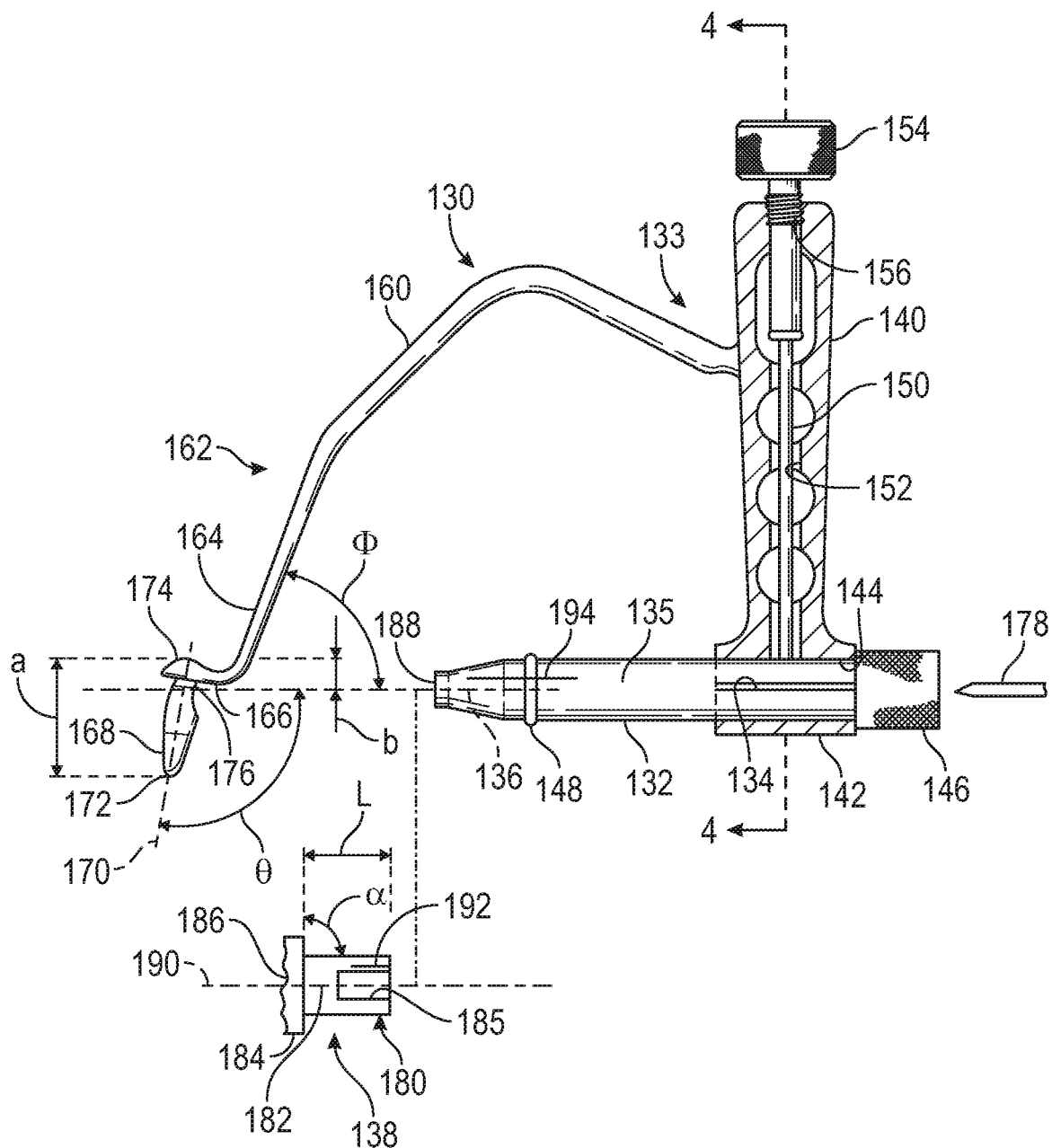
FIG. 3 is a side cross-sectional view of the patient-specific drill guide of FIGS. 1 and 2 showing a guide assembly having a positioning member and a guide arm, and a drill sleeve having a body and a patient-specific tip.
Figure 4:
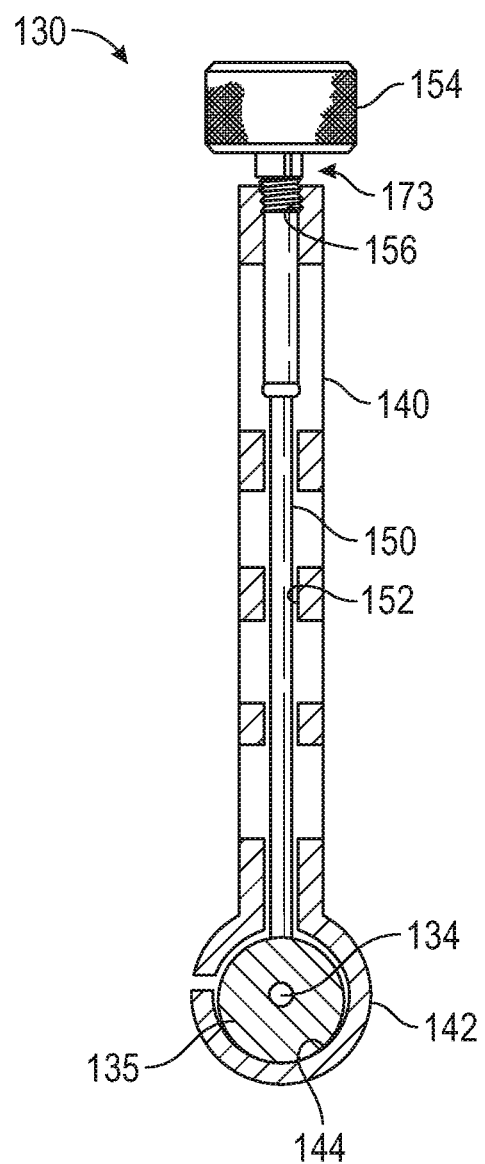
FIG. 4 is an end cross-sectional view of the positioning member of the patient-specific drill guide of FIG. 3 showing components of a securing mechanism.

FIG. 2 is a partial cutaway side view of patient-specific drill guide 130 of FIG. 1 in position for producing a tibial tunnel in a proximal end of tibia 114. FIG. 3 is a side cross-sectional view of patient-specific drill guide 130 of FIGS. 1 and 2 showing guide assembly 133 having positioning member 140 and guide arm 160, and drill sleeve 132 having body 135 and patient-specific tip 138. FIG. 4 is an end cross-sectional view of positioning member 140 of patient-specific drill guide 130 of FIG. 3 showing components of securing mechanism 173. Construction and operation of tibial drill guide 130 is discussed with concurrent reference to FIGS. 1-4.

Tibial drill guide 130 can be coupled to knee joint 110, after soft tissue has been opened, in order to facilitate an ACL procedure. Tip 172 of guide arm 160 can be inserted into femoral intercondylar notch 116 at tibial eminence 124. Tip 138 of drill sleeve 132 can be positioned against tibial 114, such as at a proximal anterior surface. The position of drill sleeve 132 in aperture 144 of collar 142 can be adjusted using knob 146. The position of drill sleeve 132 in aperture 144 can be locked using thumb screw 154. A surgeon or other practitioner can manipulate tibial drill guide 130 to locate tip 138 on a desirable location on tibia 114. As discussed herein, tip 138 can be patient-specific such that the surgeon can mate tip 138 onto a location of tibia 114 that is known to provide drill sleeve 132 with the desired orientation relative to tibial eminence 124. Tip 138 can have a patient-specific contour that is a mirror image or inverse of tibia 114 at that particular location to permit tip 138 to mate flushly on tibia 114 in only that one location. Thus, a tibial tunnel drilled using aperture 134 will have sufficient length and a desirable angle to ensure a ligament will adequately grow into tissue of tibia 114, while not being disruptive of tibial eminence 124.

Drill sleeve 132 may be of an elongated cylindrical shape, although it will be appreciated that any suitable shape may be used. Drill sleeve 132 can includes aperture 134 for allowing the passage of a suitable drilling device, such as a K-wire or drill bit 178. Aperture 134 can have an axis 136 disposed along a longitudinal axis which may be its central longitudinal axis. As mentioned, to provide means for engaging the external surface of tibia 114, drill sleeve 132 can also include a patient-specific tip 138 at its forward-most end.

Drill guide 130 can also include guide assembly 133 that can provide a multiple-point anatomical reference system for aligning drill sleeve 132 in a desired position. Guide assembly 133 can accomplish this multiple-point anatomical reference system by being able to contact several different reference points within the knee joint. Guide assembly 133 can be able to simultaneously contact trochlear groove 122, the femoral intercondylar roof disposed at the top of the femoral intercondylar notch 116 and tibial eminence 124. It will be appreciated, however, that this multiple-point reference system may contact other knee joint locations or may use other suitable reference points for aligning drill sleeve 132.

In example arrangements, guide assembly 133 can include positioning member 140 which can be in the form of an tapered elongated bar. Positioning member 140 can be of any convenient shape for ease in handling. Positioning member 140 can also include any surface irregularities or contours that facilitate gripping by hand. For example, ergonomic contours can be included to facilitate tactile gripping of a hand of a surgeon.

Drill guide 130 can be in a configuration where drill sleeve 132 is adjustable with respect to guide assembly 133, while in other patient-specific embodiments, drill sleeve 132 can be fixed to positioning member 140. Adjustability can be provided by disposing drill sleeve 132 within collar 142 attached to positioning member 140 at its lower or inferior end. Collar 142 is shown to have aperture 144 that can correspond to the configuration of drill sleeve 132. Aperture 144 can be of a substantially cylindrical configuration and can be sized to allow snug sliding movement of drill sleeve 132 in a longitudinal direction within collar 142. The axis of aperture 144 can be centrally located in collar 142 and can substantially correspond to axis 136 of drill sleeve 132. It will be appreciated, however, that the shapes of the components set forth herein may vary and may be of any suitable shape. Further, it will be appreciated that the principle of relating one or more dimensional aspects of drill sleeve 132 to guide assembly 133, and in particular to collar 142, may be accomplished while altering the shapes and dimensions of the components set forth herein.

To provide means for limiting the longitudinal travel of drill sleeve 132 within collar 142, drill guide 130 can further include forward and rear limiting devices. In this regard, drill sleeve 132 can include knob 146 located at the rearward-most end of body 135. Knob 146 can be sized to a diameter larger than that of aperture 134. This can provide an abutment surface that limits forward travel of drill sleeve 132 within aperture 134 when knob 146 abuts the rear edge of collar 142. Knob 146 may preferably have a roughened external surface for facilitating manipulation of drill sleeve 132 by hand. Drill sleeve 132 can also include o-ring 148 located proximate the forward portion of body 135 for limiting rearward travel of drill sleeve 132 within collar 142. O-ring 148 can be sized slightly larger than the diameter of drill sleeve 132. In this configuration, o-ring 148 can provide enough resistance to prevent rearward travel of drill sleeve 132 once it abuts against the forward edge of collar 142. O-ring 148 can be constructed of a compressible material such as an elastomeric rubber. Thus, o-ring 146 can be deformed sufficiently to allow drill sleeve 132 to be pulled through aperture 144 in a rearward direction along with the remainder of drill sleeve 132. This can allow drill sleeve 132 to be separated from the remainder of drill guide 130.

To provide means for securing drill sleeve 132 in a substantially stationary position within collar 142, drill guide 130 can further include securing mechanism 173 including transverse pin 150 which is located within aperture 152 of positioning member 140. Transverse pin 150 can abut against body 135 of drill sleeve 132 with force sufficient to prevent drill sleeve 132 from sliding within collar 142. To provide means for maintaining force of transverse pin 150 against drill sleeve 132, drill guide 130 can further include thumb screw 154. Thumb screw 154 can be located at the upper end of transverse pin 150. Thumb screw 154 can be threaded into corresponding threaded bore 156 disposed at the top of positioning member 132 until the distal tip of transverse pin 150 abuts drill sleeve 132 with sufficient force to hold drill sleeve 132 in a stationary position within collar 142.

To provide means for aligning drill sleeve 132 in a desired position for formation of a tibial tunnel, guide assembly 133 can further include guide arm 160. In the arrangement shown in FIGS. 1-4, guide arm 160 can be attached to positioning member 140 near its uppermost end. It will be appreciated, however, that guide arm 160 may be connected to positioning member 140 at other locations. Guide arm 160 can be attached to positioning member 140 at a patient-specific location to set distance b, shown in FIG. 3, at a patient-specific length based on a preoperative plan. Additionally, as discussed below with reference to FIG. 6, guide arm 160 can be adjustably connected to adjust distance b to a patient-specific length based on a preoperative plan. Guide arm 160 can include a guide region, generally designated by the numeral 162, which is located at the forward-most region of guide arm 160. As will be more fully discussed below, guide region 162 can be configured to provide the multiple-point reference system for aligning drill guide 130.

Figure 5:
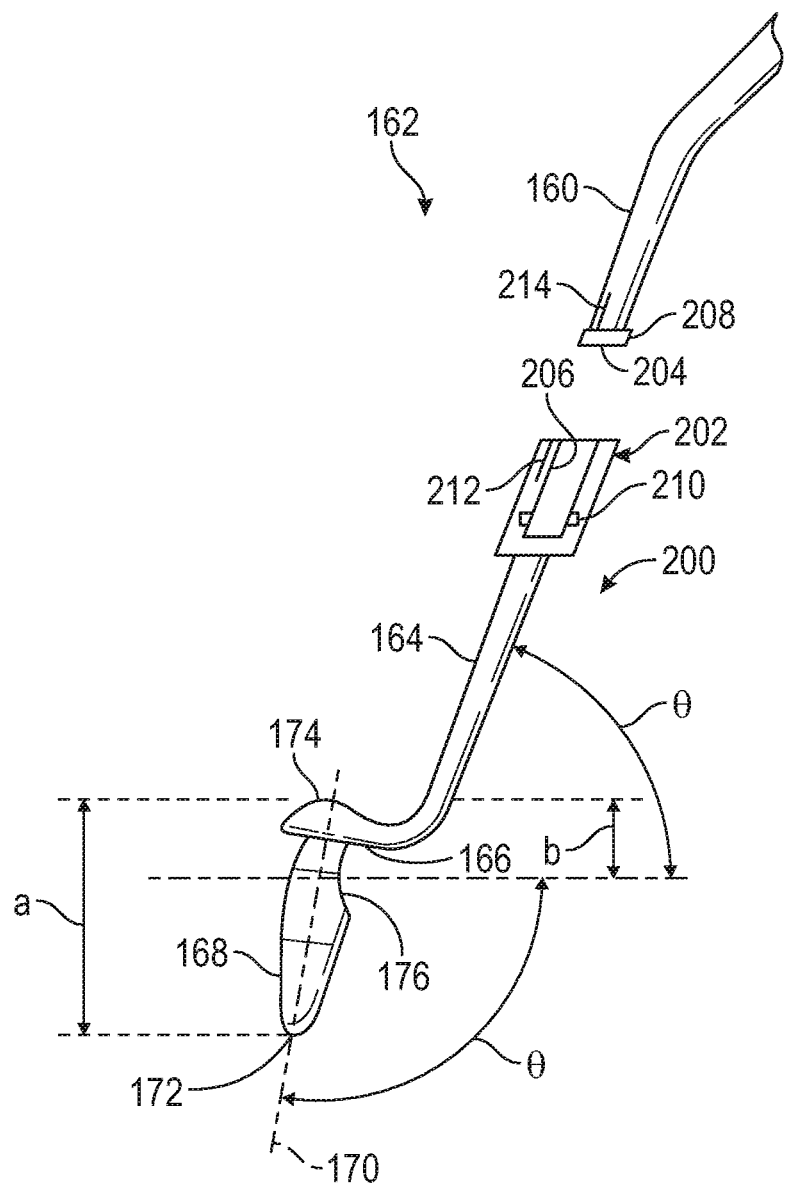
FIG. 5 is a broken away close-up view of the guide arm of FIG. 3 showing a removable patient-specific trochlear tip.

Guide region 162 of guide arm 160 can have several specialized sections that work simultaneously to accomplish the guiding procedure. These can include first guide section 164 formed as a first forward extension of guide arm 160. As shown in FIG. 5, first guide section 164 can be removably attached to guide arm 160 so that different patient-specific tips 138 can be attached to guide assembly 133. First guide section 164 can be operable to contact trochlear groove 122 of a knee joint. Second guide section 166 can be formed as another portion of guide arm 160 forward of first guide section 164. Second guide section 166 can be operable to contact the roof of femoral intercondylar notch 116. Guide region 162 can further include a third guide section, provided as extension 168, connected to second guide section 166 at its forward-most end. Extension 168 can be an elongated protuberance shaped as a cylindrical section with a cone-shaped tip that includes longitudinal axis 170. Extension 168 may be integrally formed with second guide section 166 of guide arm 160, or may alternatively be a separate element affixed to second guide section 166. First guide section 164, second guide section 166 and extension 168 can be sized and oriented in patient-specific sizes and configurations which will be described in greater detail below. Extension 168 can include three surfaces which aid in proper positioning and function of drill guide 130. These can include tip 172 located at its distal end, heel 174 located at the proximal end of extension 168 and stop 176 which is a flattened region located on the surface of extension 168 facing drill sleeve 132 in the region of axis 136. It will be appreciated that extension 168 may be integrally formed with second guide section 166 of guide arm 160. Extension 168 may also be a separate element affixed to second guide section 166, as shown in FIG. 3. Heel 174 may be either the end portion of guide arm 160 or the upper portion of extension 168. However, for purposes of simplicity and explanation, this component will be referred to as a portion of extension 168.

As shown FIG. 2, tibial drill guide 130 can perform its guiding function through the contacting of three surfaces of a knee joint. When placed in a fully inserted position with the knee in full extension or in slight hyperextension as shown in FIG. 2, tibial drill guide 130 can guide the drilling procedure by being simultaneously locked in contact with three separate points of the anatomy of knee joint 110 (e.g., trochlear groove 122, the roof of femoral intercondylar notch 116 and tibial eminence 124). In this regard, first guide section 164 can contact trochlear groove 122, while tip 172 of extension 168 contacts tibial eminence 124. At the same time, heel 174 of extension 168 can contact the roof of femoral intercondylar notch 116. First section 164 can have a patient-specific shape to match the contour of trochlear groove 122 for a specific patient, as can be determined from images taken during the preoperative planning process. Tip 172 can have a patient-specific length a, as discussed below, as can be determined from images taken during the preoperative planning process. Also, heel 174 can have a patient-specific shape to match the contour of the roof of femoral intercondylar notch 116 of a specific patient, as can be determined from images taken during the preoperative planning process.

For embodiments where patient-specific features are combined with non-patient specific or generic features, it has been found that constructing drill guide 130 to include several parameters can enhance the ability of drill guide 130 to properly locate the tibial tunnel. A first parameter is the angle θ between axis 136 and longitudinal axis 170 of extension 168. The angle θ can be approximately 100°±5°. A second parameter is the angle Φ between first guide section 164 of guide arm 160 and axis 136. This angle can be approximately 70°±5°. Another parameter is the length of extension 168, as measured in a direction perpendicular to axis 136. This parameter, represented by the letter a, can be 20 mm±5 mm. Another parameter is the distance b, measured form the uppermost point of heel 172 to axis 136. This distance can be 5 mm±3 mm.

In other examples, angle θ, angle Φ, length a, and distance b can be patient-specific parameters incorporated into the design and manufacture of drill guide 130 as fixed, patient-specific angles, lengths and distances. In additional examples, angle θ, angle Φ, length a, and distance b can adjusted to patient-specific angles, lengths and distances by adjusting the relative position of various components of drill guide 130, for example as discussed below with reference to FIGS. 5 and 6.

It will be appreciated that since the most favorable position for a tibial tunnel will depend upon the relative sizes and configurations of the femur and tibia, any or all the measurements set forth herein may be varied as necessary to determine the proper tibial tunnel location. For example, the dimensions of several or all of the components may be smaller or larger for use with smaller or larger patients. Thus, the proper size of drill guide 130 for a specific patient can be determined by reference to the preoperative plan and associated images and measurements taken therefrom of the knee joint of the specific patient. Drill guide 130 can be constructed of 17-4 stainless steel, although it will be appreciated that any suitable material may be used.

As shown in FIG. 3, tip 138 can comprise adapter 180, which can include coupler 182 and contact pad 184. Coupler 182 can include socket 185. Contact pad 184 can include patient-specific surface 186. Patient-specific surface 186 can be disposed at angle α relative to the axis of socket 185.

Contact pad 184 can comprise a surface area configured to mate with a portion of tibia 114 located near the proximal end of tibia 114 near tibial eminence 124. Contact pad 184 can envelop a surface are so that patient-specific surface 186 can uniquely mate with tibia 114. The particular size of contact pad 184 can be selected by a surgeon during the preoperative planning process to ensure engagement with landmark features identified on the tibia using the preoperative imaging.

Coupler 182 can extend from a rear surface of contact pad 184 for connecting with tip 188 of body 135 of drill sleeve 132. Coupler 182 can include socket 185 that can be sized to receive tip 188. For example, socket 185 can be sized to form a force fit or an interference fit. Additionally, tip 188 can include a lip or flange (not shown) that can seat with a corresponding groove or channel (not shown) within socket 185. In examples, adapter 180 can be constructed of a compliant material such as a polymer so that patient-specific surface 186 can be flushly mated with the contours of tibia 114 and socket 185 can yield to receive a lip or flange on tip 188. Adapter 180 can also be joined to body 135 using other suitable methods, such as threaded engagements, snap engagements, pinned engagements or the like.

Drill guide 130 can also be provided with features to ensure desired rotational alignment of adapter 180 relative to body 135. For example, coupler 182 can be provided with indicia, such as line 192 that can align with line 194 on body 135. Lines 192 and 194 can be etched into their respective components or otherwise formed therein or added thereto. For example, when lines 192 and 194 axially align, socket 185 will be properly oriented relative to trochlear tip 172 such that patient-specific surface 186 can mate with tibia 114 in the desired engagement based on the preoperative plan. Additionally, the cross-sectional shape of body 135 and socket 185 can be constructed such that adapter 180 can be assembled with body 135 in only one orientation and relative rotation therebetween is prevented.

Contact pad 184 can be connected to coupler 182 so that patient-specific surface 186 form angle α relative to axis 190 of coupler 182 and socket 185. Angle α can have a patient-specific value based on a preoperative plan to ensure that patient-specific surface 186 mates flush with tibia 114 when trochlear tip 172 is seated within the knee joint 110. Furthermore, length L of coupler 182 can be set to a patient-specific length. Also, the location of the center of contact pad 184 and patient-specific surface 186 can be offset from axis 190 a patient-specific distance.

FIG. 5 is a broken away close-up view of guide region 162 of guide arm 160 of FIG. 3 showing removable patient-specific trochlear tip 172. First guide section 164 can be separable from the remainder of guide arm 160 to form adapter 200 that can be connected to guide arm 160 via coupler 202. Trochlear tip 172 can include extension 168 that can extend along axis 170. Extension 168 can extend from first guide section 164 opposite heel 174.

Coupler 202 can extend from a rear surface of first guide section 164 for connecting with tip 204 of guide arm 160. Coupler 202 can include socket 206 that can be sized to receive tip 204. For example, socket 206 can be sized to form a force fit or an interference fit. Additionally, tip 204 can include a lip or flange 208 that can seat with a corresponding groove or channel 210 within socket 206. In examples, adapter 200 can be constructed of a compliant material such as a polymer so that socket 206 can yield to receive lip or flange 208 on tip 204. Adapter 200 can also be joined to guide arm 160 using other suitable methods, such as threaded engagements, snap engagements, pinned engagements or the like.

Drill guide 130 can also be provided with features to ensure desired rotational alignment of adapter 200 relative to guide arm 160. For example, coupler 202 can be provided with indicia, such as line 212 that can align with line 214 on guide arm 160. Lines 212 and 214 can be etched into their respective components or otherwise formed therein or added thereto. For example, when lines 212 and 214 axially align, socket 206 will be properly oriented relative to patient-specific surface 186 of tip 138 (FIG. 3). Additionally, the cross-sectional shape of guide arm 160 and socket 206 can be constructed such that adapter 200 can be assembled with guide arm 160 in only one orientation and relative rotation therebetween is prevented. Additionally, lip or flange 208 and groove or channel 210 can be provided with anti-rotation features, such as scallops or detents.

Figure 6:
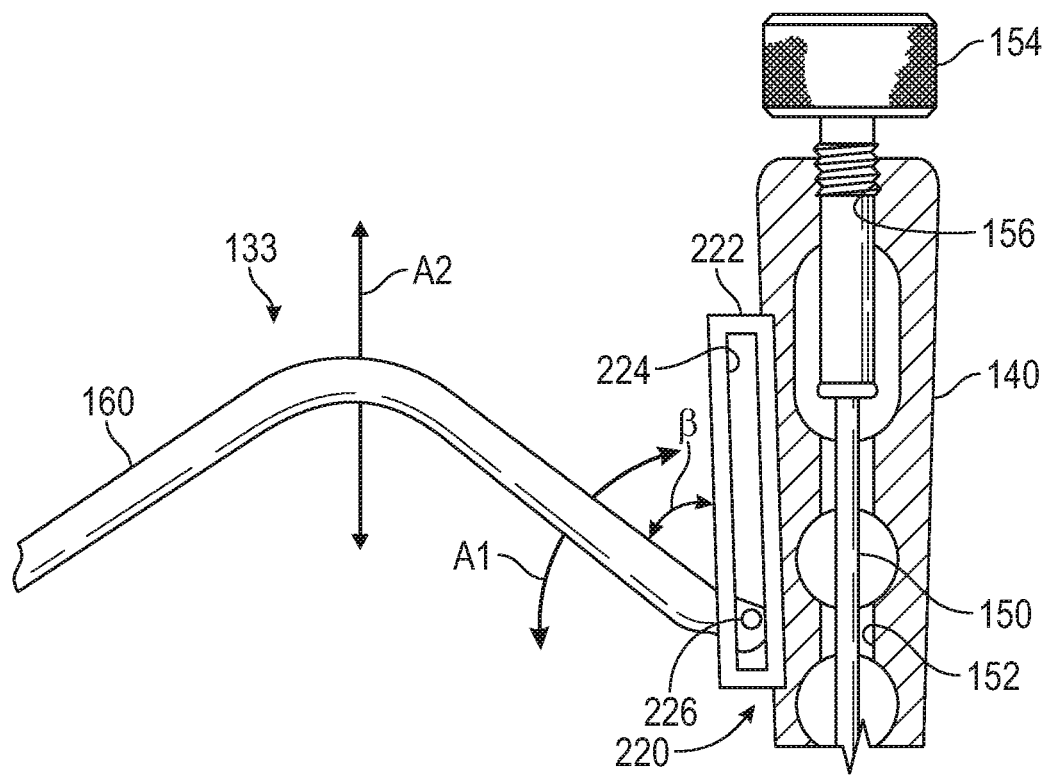
FIG. 6 is a broken away close-up view of the guide assembly of FIG. 3 showing an adjustment mechanism coupling the guide arm to the positioning member.

FIG. 6 is a broken away close-up view of guide assembly 133 of FIG. 3 showing adjustment mechanism 220 coupling guide arm 160 to positioning member 140. Adjustment mechanism 220 can include housing 222 that can include track 224 in which pin 226 can ride. Pin 226 can extend through a proximal end of guide arm 160 to pivotably couple guide arm 160 to positioning member 140 to adjust angle β, as shown by arrows A1. The position of pin 226 within track 224 can also be vertically adjusted to adjust the relative position between guide arm 160 and positioning member 140, as shown by arrows A2. Pin 226 can comprise a threaded fastener that can extend through a through-bore or threaded bore in guide arm 160. A securing member, such as a nut, can be engaged with pin 226 to lock guide arm 160 into a desired angular position and vertical position. Adjustment of angle θ and the vertical position of guide arm 160 can change angle θ, angle Φ and distance b shown in FIG. 3. Adjustment of the vertical position of guide arm 160 can change distance b shown in FIG. 3. Angle β, angle θ, angle Φ and distance b can be adjusted to fit a specific patient as can be determined from a preoperative plan. Furthermore, in various examples, angle β, angle θ, angle Φ, length a, distance b, angle α, and length L, and other features, can be combined in any combination of patient-specific and patient-generic geometries to achieve the desired fit on a specific patient based on the preoperative plan.

Figure 7:
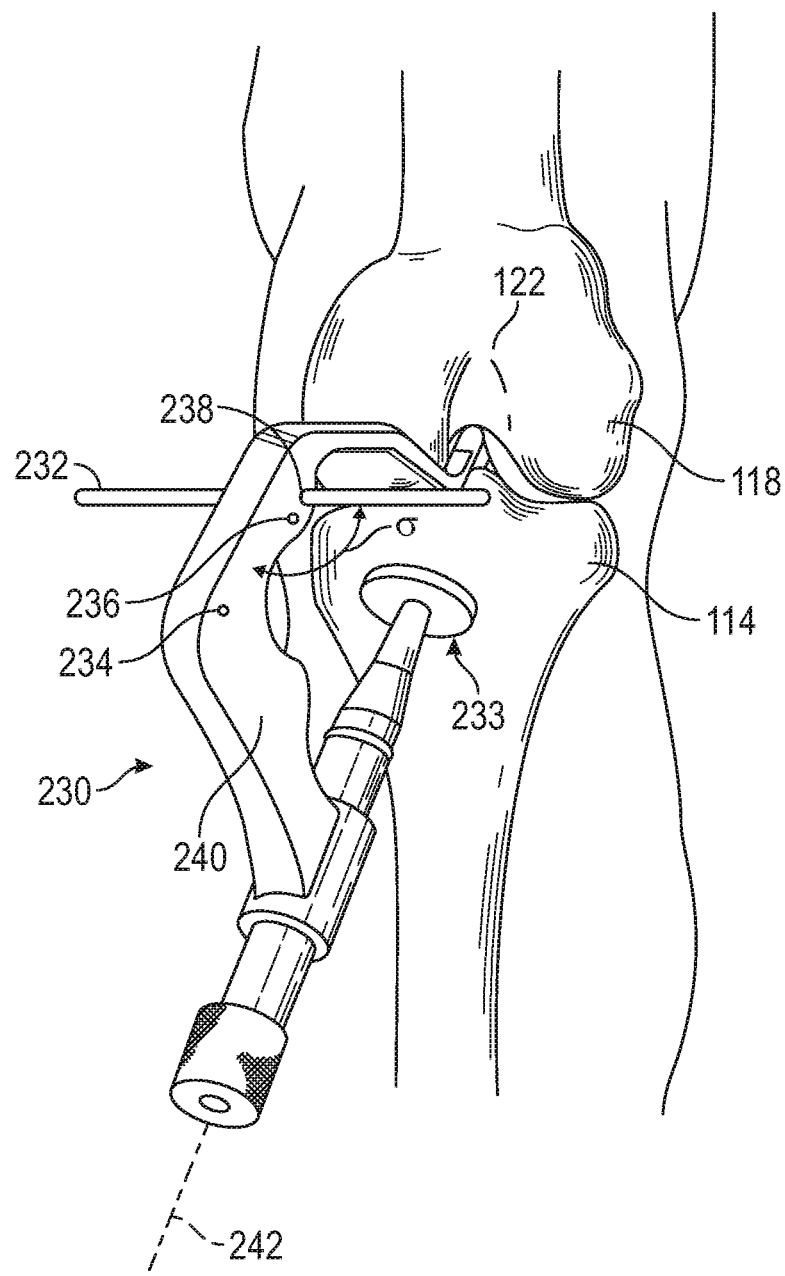
FIG. 7 is a perspective view of another embodiment of a patient-specific drill guide including a guide rod that can be used to align the patient-specific drill guide with a tibia.

FIG. 7 is a perspective view of patient-specific drill guide 230 including guide rod 232 that can be used to align patient-specific drill guide 230 with tibia 114. Drill guide 230 can include patient-specific tip 233 and can be configured to operate similarly to each and all of the various embodiments and examples of drill guide 130 described herein. Patient-specific drill guide 230 can include guide rod 232 that can be passed through bores 234, 236 and 238 in body 240 of drill guide 230. Body 240 can function similarly to positioning member 140 of drill guide 130. Bores 234, 236 and 238 can pass through body with particular orientations to allow guide rod 232 to be disposed relative to the axes and faces of body 240 in specific orientations so that a surgeon can have a visual indication of the alignment of body 240 with respect to tibia 114. For example, bore 234 can be orientated substantially orthogonal to drill axis 242 and substantially parallel to the transverse plane. Bores 236 and 238 can be used for left and right sides of the patient. Bores 236 and 238 can also be configured to positon guide rod 232 parallel to the transverse plane, but with particular anteversion and retreversion angles to align guide rod 232 with the coronal plane for left and right knee joints. For example, guide bar 232 can be disposed at an angle σ of approximately 70 degrees (or 110 degrees) relative to body 140 in opposite orientations for bores 236 and 238, while bore 234 positions guide bar 232 such that angle σ is approximately 90 degrees.

Figure 8:
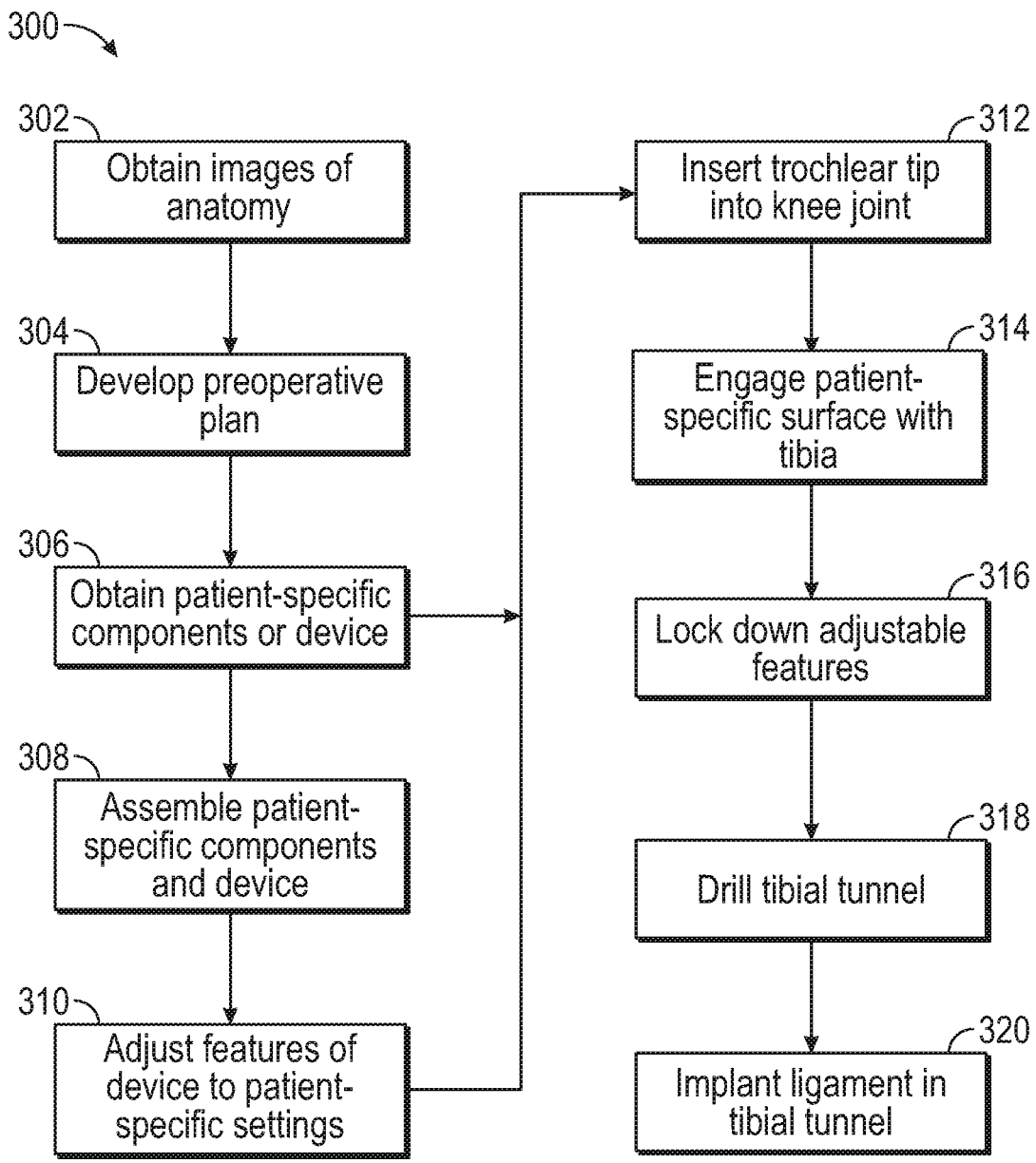
FIG. 8 is a line diagram illustrating steps of a method for performing an anterior cruciate ligament replacement, reconstruction or pair procedure using the preoperative planning procedures and patient-specific devices described herein.

FIG. 8 is a line diagram illustrating steps of method 300 for performing an anterior cruciate ligament (ACL) replacement, reconstruction or pair procedure using the preoperative planning procedures and patient-specific devices described herein. At step 302, images of the anatomy of a patient can be obtained. The images can be taken using any of the aforementioned imaging techniques, such as MRI, CT, ultrasound, X-ray and the like. The images can include various views of a knee joint of the patient such that specific measurements of the joint can be measured or otherwise determined. The images can be taken at the same facility the ACL procedure is to be performed or at a different facility and can be taken in advance of the procedure or contemporaneously, e.g., just prior to the procedure. The images can be digitized and transmitted for viewing by a surgeon for development of a preoperative plan at step 304. The preoperative plan can be constructed using computer hardware and software as are known in the art. The preoperative plan can be used to determine the location, size and orientation of a tibial tunnel to be used in the repair procedure to, among other things, ensure adequate length for osseointegration of the repair ligament and prevent disturbing features of the tibia such as the tibial eminence. For example, the angle of the tibial tunnel relative to the mechanical or anatomic axis of the tibia can be determined, the entry point of the tibial tunnel on an anterior surface of the tibia for placement of a patient-specific drill sleeve, such as drill sleeve 132, can be determined, and the exit point of the tibial tunnel relative to a tibial eminence can be determined. Furthermore, angles, lengths and distances of a patient-specific drill guide, such as drill guide 130, can be determined.

At step 306, patient-specific components and devices can be obtained. The components and devices can be obtained by purchase, such as by providing manufacturing instructions based on the preoperative plan to a manufacturing facility. The components and devices can be obtained by direct manufacture at a medical facility, such as by use of additive manufacturing processes. Example patient-specific components can include adapter 180 and adapter 200. An example patient specific device includes drill guide 130 where the geometry of tip 172, angle θ and angle Φ, for example, are fixed at patient-specific values. At step 308, the patient-specific components and devices can be assembled if they are provided as separate pieces. That is, patient-specific adapters can be assembled to standard or patient-generic guides. At step 310, any adjustable features of the device can be setup for use with a specific patient. That is, for example, sliding and pivoting components (e.g., adjustment mechanism 220, adapter 180 and adapter 200) of an adjustable device can be set according to a preoperative plan for use with a specific patient. However, a fully patient-specific device that is not adjustable, customizable or reusable can be provided such that assembly and adjustment is not needed. In such case, method 300 can proceed from step 306 directly to step 312.

At step 312, surgical steps to begin the ACL reconstruction can begin, including preparation of the knee joint to receive the patient-specific tibial drill guides described here. For example, soft tissue covering the knee joint can be removed or retracted to expose the distal end of the femur and the proximal end of the tibia. In particular, at step 312, a trochlear tip, such as tip 172, can be inserted between the intercondylar roof of the femur and the tibial eminence of the tibia. Additionally, patient specific surfaces of tip 172, such as at heel 174, can be mated with the intercondylar roof. At step 314, a patient-specific surface of the drill guide, such as tips 138 and 233, can be engaged with an anterior surface of the tibia to align a drill sleeve for placing the tibial tunnel. For example, the patient-specific surface can be placed on the anterior surface of the tibia a distance below the articulating surfaces of the tibia and in line with the tibial eminence. The patient-specific surface can be moved into position by translating different components of the drill guide (e.g., body 135 and collar 142) relative to each other until the patient-specific surface flushly contacts the tibia. At step 316, any adjustable features of the drill guide can be locked down after fit of the drill guide is confirmed. That is, the drill sleeve can be locked into position relative to a remainder of the drill guide using securing mechanism 173, for example, and any other patient-specific angles and distances between components of the drill guide can be confirmed and locked down before the tibial tunnel is drilled. At step 318, the tibial tunnel can be produced by insertion of a drill bit or a pin into the drill sleeve, such as at aperture 134. The drill guide can then be removed from the knee joint. At step 320, the ACL repair procedure can be conventionally performed to implant a reconstructed ACL ligament using the tibial tunnel placed with the patient-specific drill guide.

After the surgery, a fully patient-specific drill guide can be disposed of according to customary practice. For partially patient-specific drill guides, patient-specific components can be removed and disposed of, and the patient-generic or adjustable drill guide can be sterilized for use with another patient using a different patient-specific adapter or component.

The patient-specific drill guides of the present application are can assist in effectively placing tibial tunnels in tibia bones to optimize integration of the reconstructed ACL in the tibia and optimize functioning of the repaired ACL joint. For example, proper placement of the tibia tunnel on the tibia provides a bone bore of suitable length for allowing the ligament to grow into the bone. Longer tunnels are more effective in providing additional bonding to the bone. However, the tibial tunnel must also be placed at an angle suitable to allow the ACL to adequately flex and stretch while the knee joint operates without rubbing or binding of the ACL against surfaces of the tibia. Furthermore, the tibial tunnel should not improperly diminish the tibial eminence. The preoperative planning procedures described herein can permit a surgeon to preoperatively determine the location of the tibial tunnel in the tibia to achieve these and other benefits. The patient-specific drill guides described herein can permit a surgeon to properly place the drill guide intraoperatively in order to ensure the tibial tunnel is drilled according to the preoperative plan.

VARIOUS NOTES & EXAMPLES

Example 1 can include or use subject matter such as a drill guide for use in drilling a tibial tunnel in a knee joint having a femur with an intercondylar roof and a trochlear groove, and a tibia having a tibial eminence, said drill guide can comprise a guide assembly and a drill sleeve. The guide assembly can comprise a positioning member including an inferior end, and a guide arm extending from the positioning member and including a trochlear tip for engaging the intercondylar roof. The drill sleeve can comprise a body attached to the inferior end, an aperture extending along a drilling axis of the body, and a distal end having a patient-specific surface configured to engage an anterior surface of the tibia inferior of the tibial eminence.

Example 2 can include, or can optionally be combined with the subject matter of Example 1, to optionally include a patient-specific surface that can comprise a three-dimensionally curved surface configured to mate with the anterior surface of the tibia in only one position.

Example 3 can include, or can optionally be combined with the subject matter of one or any combination of Examples 1 or 2 to optionally include a distal end that can comprise a removable tip including the patient-specific surface.

Example 4 can include, or can optionally be combined with the subject matter of one or any combination of Examples 1 through 3 to optionally include a removable tip that can comprise an adapter couplable to the distal end of the drill sleeve, the adapter can comprise a pad portion having the patient-specific surface, and an attachment portion configured to attach to the body.

Example 5 can include, or can optionally be combined with the subject matter of one or any combination of Examples 1 through 4 to optionally include a trochlear tip that can include a bulbous heel positioned opposite a distal tip, the bulbous heel being operable to contact the intercondylar roof of the femur.

Example 6 can include, or can optionally be combined with the subject matter of one or any combination of Examples 1 through 5 to optionally include a bulbous heel that can include an intercondylar roof surface that is patient-specific to include a three-dimensionally curved surface configured to mate with the intercondylar roof in only one position.

Example 7 can include, or can optionally be combined with the subject matter of one or any combination of Examples 1 through 6 to optionally include a distance between a major axis of the body of the drill sleeve and the bulbous heel that can be fixed at a patient-specific length.

Example 8 can include, or can optionally be combined with the subject matter of one or any combination of Examples 1 through 7 to optionally include a distance between the trochlear tip and the distal end that can be adjustable.

Example 9 can include, or can optionally be combined with the subject matter of one or any combination of Examples 1 through 8 to optionally include a securing mechanism that can be operable to immobilize the body of the drill sleeve relative to the inferior end of the positioning member.

Example 10 can include, or can optionally be combined with the subject matter of one or any combination of Examples 1 through 9 to optionally include a distance between the trochlear tip and the distal end that can be fixed at a patient-specific length.

Example 11 can include, or can optionally be combined with the subject matter of one or any combination of Examples 1 through 10 to optionally include an angle between a major axis of the trochlear tip and a major axis of the body of the drill sleeve that can be set to a patient-specific angle.

Example 12 can include, or can optionally be combined with the subject matter of one or any combination of Examples 1 through 11 to optionally include a position of the positioning member that can be adjustable relative to the guide arm.

Example 13 can include, or can optionally be combined with the subject matter of one or any combination of Examples 1 through 12 to optionally include a guide bar that can extend through the guide assembly transverse to the body of the drill sleeve.

Example 14 can include or use subject matter such as a method of producing a tibial tunnel for an anterior cruciate ligament reconstruction surgery using a patient-specific drill guide, the method can comprise inserting a trochlear tip of a guide arm between a tibial eminence of a tibia and an intercondylar roof of a femur, adjusting a position of a positioning member connected to the guide arm proximate a proximal end of the tibia, engaging a patient-specific tip of a drill sleeve connected to the positioning member with a portion of an anterior surface of the tibia proximate the tibial eminence, and inserting a drill bit through the drill sleeve to drill a tibial tunnel in the tibia.

Example 15 can include, or can optionally be combined with the subject matter of Example 14, to optionally include a patient-specific tip that can include a three-dimensionally curved surface configured to mate with the portion of the anterior surface of the tibia in only one position.

Example 16 can include, or can optionally be combined with the subject matter of one or any combination of Examples 14 or 15 to optionally include attaching an adapter to the drill sleeve to connect the patient-specific tip to the drill sleeve.

Example 17 can include, or can optionally be combined with the subject matter of one or any combination of Examples 14 through 16 to optionally include inserting the trochlear tip between the tibial eminence and the intercondylar roof that can comprise engaging a patient-specific trochlear surface of the trochlear tip with the intercondylar roof.

Example 18 can include, or can optionally be combined with the subject matter of one or any combination of Examples 14 through 17 to optionally include inserting a guide bar into the positioning member, and aligning the drill sleeve with the tibia using the guide bar.

Example 19 can include, or can optionally be combined with the subject matter of one or any combination of Examples 14 through 18 to optionally include adjusting a position of at least one of the guide arm relative to the positioning member and the drill sleeve relative to the positioning member based on a pre-operative plan of a specific patient to match dimensions of the patient-specific drill guide to the specific patient.

Example 20 can include, or can optionally be combined with the subject matter of one or any combination of Examples 14 through 19 to optionally include adjusting a position of the guide arm relative to the positioning member to adjust at least one of a distance between the trochlear tip and the patient-specific tip and an angle between the trochlear tip and the drill sleeve.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A drill guide for use in drilling a tibial tunnel in a knee joint having a femur with an intercondylar roof and a trochlear groove, and a tibia having a tibial eminence, said drill guide comprising:
    a guide assembly comprising:
        a positioning member including an inferior end; and
        a guide arm extending from the positioning member and including a trochlear tip for engaging the intercondylar roof; and
    a drill sleeve comprising:
        a body attached to the inferior end;
        an aperture extending along a drilling axis of the body; and
        a distal end having a patient-specific surface configured to engage an anterior surface of the tibia inferior of the tibial eminence, wherein the distal end comprises a removable tip including the patient-specific surface, the removable tip comprising an adapter couplable to the distal end of the drill sleeve, the adapter comprising:
            a pad portion having the patient-specific surface; and an attachment portion configured to attach to the body.

2. The drill guide of claim 1, wherein the patient-specific surface comprises a three-dimensionally curved surface configured to mate with the anterior surface of the tibia in only one position.

3. The drill guide of claim 1, wherein the trochlear tip includes a bulbous heel positioned opposite a distal tip, the bulbous heel being operable to contact the intercondylar roof of the femur.

4. The drill guide of claim 3, wherein the bulbous heel includes an intercondylar roof surface that is patient-specific to include a three-dimensionally curved surface configured to mate with the intercondylar roof in only one position.

5. The drill guide of claim 3, wherein a distance between a major axis of the body of the drill sleeve and the bulbous heel is fixed at a patient-specific length.

6. The drill guide of claim 1, wherein a distance between the trochlear tip and the distal end is adjustable.

7. The drill guide of claim 6, further comprising a securing mechanism operable to immobilize the body of the drill sleeve relative to the inferior end of the positioning member.

8. The drill guide of claim 1, wherein a distance between the trochlear tip and the distal end is fixed at a patient-specific length.

9. The drill guide of claim 1, wherein an angle between a major axis of the trochlear tip and a major axis of the body of the drill sleeve is set to a patient-specific angle.

10. The drill guide of claim 1, wherein a position of the positioning member is adjustable relative to the guide arm.

11. The drill guide of claim 10, further comprising an adjustment mechanism that couples the guide arm to the positioning member, the adjustment mechanism comprising:
 a pin located at a proximal end of the guide arm; and
 a housing including a track in which the pin can ride;
 wherein the pin can ride vertically in the track to vertically adjust the relative position of the guide arm and positioning member and the guide arm can pivot about the pin to adjust the angle between the guide arm and the housing.

12. The drill guide of claim 1, further comprising a guide bar extending through the guide assembly transverse to the body of the drill sleeve.

13. The drill guide of claim 1, wherein the arm comprises a first guide section that is separable from the remainder of the guide arm to form an adapter that can be connected to the guide arm via a coupler such that the trochlear tip is separable from the guide arm, wherein the coupler extends from a rear surface of the first guide section for connecting with a tip of the remainder of the guide arm.

14. A drill guide for use in drilling a tibial tunnel in a knee joint having a femur with an intercondylar roof and a trochlear groove, and a tibia having a tibial eminence, said drill guide comprising:
 a guide assembly comprising:
  a positioning member including an inferior end; and
  a guide arm extending from the positioning member and including a trochlear tip for engaging the intercondylar roof, the guide arm comprising:
   a first guide section that is separable form the remainder of the guide arm to form an adapter that can be connected to the guide arm via a coupler such that the trochlear tip is separable from the guide arm;
   wherein the coupler extends from a rear surface of the first guide section for connecting with a tip of the remainder of the guide arm; and
 a drill sleeve comprising:
  a body attached to the inferior end;
  an aperture extending along a drilling axis of the body; and
  a distal end having a patient-specific surface configured to engage an anterior surface of the tibia inferior of the tibial eminence.

15. A drill guide for use in drilling a tibial tunnel in a knee joint having a femur with an intercondylar roof and a trochlear groove, and a tibia having a tibial eminence, said drill guide comprising:
 a guide assembly comprising:
  a positioning member including an inferior end; and
  a guide arm extending from the positioning member and including a trochlear tip for engaging the intercondylar roof;
  a adjustment mechanism that couples the guide arm to the positioning member such that positioning therebetween is adjustable, the adjustment mechanism comprising:
   a pin located at a proximal end of the guide arm; and
   a housing including a track in which the pin can ride;
   wherein the pin can ride vertically in the track to vertically adjust the relative position of the guide arm and positioning member and the guide arm can pivot about the pin to adjust the angle between the guide arm and the housing; and
 a drill sleeve comprising:
  a body attached to the inferior end;
  an aperture extending along a drilling axis of the body; and
  a distal end having a patient-specific surface configured to engage an anterior surface of the tibia inferior of the tibial eminence.

* * * * *